United States Patent [19]

Muller

[11] Patent Number: 5,463,063
[45] Date of Patent: Oct. 31, 1995

[54] RING CLOSURE OF N-PHTHALOYLGLUTAMINES

[75] Inventor: George W. Muller, Bridgewater, N.J.

[73] Assignee: Celgene Corporation, Warren, N.J.

[21] Appl. No.: 140,237

[22] Filed: Oct. 20, 1993

Related U.S. Application Data

[63] Continuation-in-part of Ser. No. 87,510, Jul. 2, 1993, abandoned.

[51] Int. Cl.$^6$ .................................................. C07D 401/04
[52] U.S. Cl. ......................... 546/201; 528/331; 528/317
[58] Field of Search ........................ 546/201; 528/331, 528/317

OTHER PUBLICATIONS

Fieser, Louis F., *Experiments in Organic Chemistry*, 3rd edition, p. 75, 1955.
J. C. Craig, "Absolute Configuration...", *J Org Chem*, vol. 53, pp. 1167–1170, 1988.

*Primary Examiner*—C. Warren Ivy
*Assistant Examiner*—D. Margaret M. Mach
*Attorney, Agent, or Firm*—Mathews, Woodbridge & Collins

[57] ABSTRACT

Cyclic imides are inhibitors of tumor necrosis factor α and can be used to combat cachexia, endotoxic shock, and retrovirus replication. A typical embodiment is 2-(2,6-dioxo-3-piperidinyl)-4-azaisoindoline-1,3-dione.

1 Claim, No Drawings

5,463,063

1

RING CLOSURE OF N-PHTHALOYLGLUTAMINES

CROSS REFERENCE TO RELATED APPLICATION

This is a continuation-in-part of Ser. No. 08/087,510 filed Jul. 2, 1993 now abandoned, the disclosure of which is incorporated herein by reference.

BACKGROUND OF THE INVENTION

The present invention relates a method of reducing levels of $TNF_\alpha$ in a mammal and to compounds and compositions useful therein.

$TNF_\alpha$, or tumor necrosis factor α, is a cytokine which is released primarily by mononuclear phagocytes in response to various immunostimulators. Excessive or unregulated $TNF_\alpha$ production has been implicated in a number of disease conditions. These include endotoxemia and/or toxic shock syndrome (Tracey et al., *Nature* 330, 662–664 (1987) and Hinshaw et al., *Circ. Shock* 30, 279–292 (1990)); cachexia (Dezube et al., *Lancet*, 335 (8690), 662 (1990)); and Adult Respiratory Distress Syndrome where $TNF_\alpha$ concentration in excess of 12,00 pg/ml have been detected in pulmonary aspirates from ARDS patients {Millar et al., *Lancet* 2(8665), 712–714 (1989)}. Systemic infusion of recombinant $TNF_\alpha$ also resulted in changes typically seen in ARDS {Ferrai-Baliviera et al., *Arch. Surg.* 124(12), 1400–1405 (1989)}.

$TNF_\alpha$ appears to be involved in bone resorption diseases, including arthritis where it has been determined that when activated, leukocytes will produce a bone-resorbing activity, and data suggest that $TNF_\alpha$ contributes to this activity. {Bertolini et al., *Nature* 319, 516–518 (1986) and Johnson et al., *Endocrinology* 124(3), 1424–1427 (1989).} It has been determined that $TNF_\alpha$ stimulates bone resorption and inhibits bone formation in vitro and in vivo through stimulation of osteoclast formation and activation combined with inhibition of osteoblast function. Although $TNF_\alpha$ may be involved in many bone resorption diseases, including arthritis, the most compelling link with disease is the association between production of $TNF_\alpha$ by tumor or host tissues and malignancy associated hypercalcemia {*Calci. Tissue Int.* (US) 46(Suppl.), S3–10 (1990)}. In Graft versus Host Reaction, increased serum $TNF_\alpha$ levels have been associated with major complication following acute allogenic bone marrow transplants {Holler et al., *Blood*, 75(4), 1011–1016 (1990)}.

Cerebral malaria is a lethal hyperacute neurological syndrome associated with high blood levels of $TNF_\alpha$ and the most severe complication occurring in malaria patients. Levels of serum $TNF_\alpha$ correlated directly with the severity of disease and the prognosis in patients with acute malaria attacks {Grau et al., *N. Engl. J. Med.* 320(24), 1586–1591 (1989)}.

$TNF_\alpha$ also plays a role is the area of chronic pulmonary inflammatory diseases. The deposition of silica particles leads to silicosis, a disease of progressive respiratory failure caused by a fibrotic reaction. Antibody to $TNF_\alpha$ completely blocked the silica-induced lung fibrosis in mice {Pignet et al., *Nature*, 344:245–247 (1990)}. High levels of $TNF_\alpha$ production (in the serum and in isolated macrophages) have been demonstrated in animal models of silica and asbestos induced fibrosis {Bissonnette et al., *Inflammation* 13(3), 329–339 (1989)}. Alveolar macrophages from pulmonary sarcoidosis patients have also been found to spontaneously release massive quantities of $TNF_\alpha$ as compared with macrophages from normal donors {Baughman et al., *J. Lab. Clin. Med.* 115(1), 36–42. (1990)}. $TNF_\alpha$ is also implicated in the inflammatory response which follows reperfusion, called reperfusion injury, and is a major cause of tissue damage after loss of blood flow {Vedder et al., *PNAS* 87, 2643–2646 (1990)). $TNF_\alpha$ also alters the properties of endothelial cells and has various pro-coagulant activities, such as producing an increase in tissue factor pro-coagulant activity and suppression of the anticoagulant protein C pathway as well as down-regulating the expression of thrombomodulin {Sherry et al., *J. Cell Biol.* 107, 1269–1277 (1988)}. $TNF_\alpha$ has pro-inflammatory activities which together with its early production (during the initial stage of an inflammatory event) make it a likely mediator of tissue injury in several important disorders including but not limited to, myocardial infarction, stroke and circulatory shock. Of specific importance may be $TNF_\alpha$-induced expression of adhesion molecules, such as intercellular adhesion molecule (ICAM) or endothelial leukocyte adhesion molecule (ELAM) on endothelial cells {Munro et al., *Am. J. Path.* 135(1), 121–132 (1989)}.

Moreover, it now is known that $TNF_\alpha$ is a potent activator of retrovirus replication including activation of HIV-1. {Duh et al., *Proc. Nat. Acad. Sci.* 86, 5974–5978 (1989); Poll et al., *Proc. Nat. Acad. Sci.* 87, 782–785 (1990); Monto et al., *Blood* 79, 2670 (1990); Clouse et al., *J. Immunol.* 142, 431–438 (1989); Poll et al., *AIDS Res. Hum. Retrovirus*, 191–197 (1992)}. At least three types or strains of HIV have been identified, i.e., HIV-1, HIV-2 and HIV-3. As a consequence of HIV infection, T-cell mediated immunity is impaired and infected individuals manifest severe opportunistic infections and/or unusual neoplasms. HIV entry into the T lymphocyte requires T lymphocyte activation. Other viruses, such as HIV-1, HIV-2 infect T lymphocytes after T cell activation and such virus protein expression and/or replication is mediated or maintained by this T cell activation. Once an activated T lymphocyte is infected with HIV, the T lymphocyte must continue to be maintained in an activated state to permit HIV gene expression and/or HIV replication. Monokines, specifically $TNF_\alpha$, are implicated in activated T-cell mediated HIV protein expression and/or virus replication by playing a role in maintaining T lymphocyte activation.

AIDS results from the infection of T lymphocytes with Human Immunodeficiency Virus (HIV). At least three types or strains of HIV have been identified, i.e., HIV-1, HIV-2 and HIV-3. As a consequence of HIV infection, T-cell mediated immunity is impaired and infected individuals manifest severe opportunistic infections and/or unusual neoplasms. HIV entry into the T lymphocyte requires T lymphocyte activation. Other viruses, such as HIV-1, HIV-2 infect T lymphocytes after T cell activation and such virus protein expression and/or replication is mediated or maintained by such T cell activation. Once an activated T lymphocyte is infected with HIV, the T lymphocyte must continue to be maintained in an activated state to permit HIV gene expression and/or HIV replication. Monokines, specifically $TNF_\alpha$, are implicated in activated T-cell mediated HIV protein expression and/or virus replication by playing a role in maintaining T lymphocyte activation. Therefore, interference with monokine activity such as by inhibition of monokine production, notably $TNF_\alpha$, in an HIV-infected individual aids in limiting the maintenance of T lymphocyte caused by HIV infection. Monocytes, macrophages, and related cells, such as kupffer and glial cells, have also been implicated in maintenance of the HIV infection. These cells, like T cells, are targets for viral replication and the level of viral replication is dependent upon the activation state of the cells. (Rosenberg et al., *The Immunopathogenesis of HIV*

*Infection, Advances in Immunology,* 57 (1989)). Monokines, such as $TNF_\alpha$, have been shown to activate HIV replication in monocytes and/or macrophages {Poli et al. *Proc. Natl. Acad. Sci.,* 87, 782–784 (1990)}, therefore, inhibition of monokine production or activity aids in limiting HIV progression as stated above for T cells. Additional studies have identified $TNF_\alpha$ as a common factor in the activation of HIV in vitro and has provided a clear mechanism of action via a nuclear regulatory protein found in the cytoplasm of cells (Osborn, et al., *PNAS* 86 2336–2340). This evidence suggests that a reduction of $TNF_\alpha$ synthesis may have an antiviral effect in HIV infections, by reducing the transcription and thus virus production.

AIDS viral replication of latent HIV in T cell and macrophage lines can be induced by $TNF_\alpha$ {Folks et al., *PNAS* 86, 2365–2368 (1989)). A molecular mechanism for the virus inducing activity is suggested by $TNF_\alpha$'s ability to activate a gene regulatory protein (NFkB) found in the cytoplasm of cells, which promotes HIV replication through binding to a viral regulatory gene sequence (LTR) {Osborn et al., *PNAS* 86, 2336–2340 (1989)). $TNF_\alpha$ in AIDS associated cachexia is suggested by elevated serum $TNF_\alpha$ and high levels of spontaneous $TNF_\alpha$ production in peripheral blood monocytes from patients {Wright et al. *J. Immunol.* 141(1), 99–104 (1988)}.

$TNF_\alpha$ has been implicated in various roles with other viral infections, such as the cytomegalia virus (CMV), influenza virus, adenovirus, and the herpes family of viruses for similar reasons as those noted.

Efforts directed to the suppression of the effects of $TNF_\alpha$ have ranged from the utilization of steroids such as dexamethasone and prednisolone to the use of both polyclonal and monoclonal antibodies {Beutler et al., Science 234, 470–474 (1985); WO 92/11383 }.

DETAILED DESCRIPTION

The present invention is based on the discovery that a class of non-polypeptide imides more fully described herein appear to inhibit the action of $TNF_\alpha$.

A first aspect of the present invention pertains to compounds of the formula:

$$Z-CH(-C_nH_{2n}-)-\overset{O}{\underset{\|}{C}}-NH-\overset{O}{\underset{\|}{C}} \qquad \text{I.}$$

in which Z is $$R^1-\overset{O}{\underset{\|}{C}}-N(-R^2-)-, \quad R^3-\overset{O}{\underset{\|}{C}}-NH-, \quad \text{or} \quad R^4-$$

in which $R^1$ is the divalent residue of (i) pyridine, (ii) pyrrolidine, (iii) imidizole, (iv) naphthalene, (v) thiophene, or (vi) a straight or branched alkane of 2 to 6 carbon atoms, unsubstituted or substituted with phenyl or phenyl substituted with nitro, cyano, trifluoromethyl, carbethoxy, carbomethoxy, carbopropoxy, acetyl, carbamyl, acetoxy, carboxy, hydroxy, amino, alkyl of 1 to 4 carbon atoms, alkoxy of 1 to 4 carbon atoms, or halo, wherein the divalent bonds of said residue are on vicinal ring carbon atoms;

$R^2$ is $-CO-$ or $-SO_2-$;

$R^3$ is (i) phenyl substituted with nitro, cyano, trifluoromethyl, carbethoxy, carbomethoxy, carbopropoxy, acetyl, carbamoyl, acetoxy, carboxy, hydroxy, amino, alkyl of 1 to 4 carbon atoms, alkoxy of 1 to 4 carbon atoms, or halo, (ii) pyridyl, (iii) pyrrolyl, (iv) imidazolyl, (v) naphthyl, (vi) thienyl, (vii) quinolyl, (viii) furyl, or (ix) indolyl;

$R^4$ is alanyl, arginyl, glycyl, phenylglycyl, histidyl, leucyl, isoleucyl, lysyl, methionyl, prolyl, sarcosyl, seryl, homoseryl, threonyl, thyronyl, tyrosyl, valyl, benzimidol-2-yl, benzoxazol-2-yl, phenylsulfonyl, methylphenylsulfonyl, or phenylcarbamoyl; and n has a value of 1, 2, or 3.

More particularly, a first preferred subclass pertains to compounds of the formula:

$$R^1-\overset{O}{\underset{\|}{C}}-N(-R^2-)-CH(-(C_nH_{2n})-)-\overset{O}{\underset{\|}{C}}-NH-\overset{O}{\underset{\|}{C}} \qquad \text{IA.}$$

in which $R^1$ is the divalent residue of (i) pyridine, (ii) pyrrolidine, (iii) imidizole, (iv) naphthalene, (v) thiophene, or (vi) a straight or branched alkane of 2 to 6 carbon atoms, unsubstituted or substituted with phenyl or phenyl substituted with nitro, cyano, trifluoromethyl, carbethoxy, carbomethoxy, carbopropoxy, acetyl, carbamyl, acetoxy, carboxy, hydroxy, amino, alkyl of 1 to 4 carbon atoms, alkoxy of 1 to 4 carbon atoms, or halo, wherein the divalent bonds of said residue are on vicinal ring carbon atoms; $R^2$ is $-CO-$ or $-SO2-$; and n has a value of 1, 2, or 3.

Preferred compounds of Formula IA include those in which $R^1$ is a divalent residue of pyridine, naphthalene or imidazole, $R^2$ is $-CO-$, and n is 2.

A second preferred subclass pertains to compounds of the formula:

$$R^3-\overset{O}{\underset{\|}{C}}-NH-CH(-(C_nH_{2n})-)-\overset{O}{\underset{\|}{C}}-NH-\overset{O}{\underset{\|}{C}} \qquad \text{IB.}$$

in which $R^3$ is (i) phenyl substituted with nitro, cyano, trifluoromethyl, carbethoxy, carbomethoxy, carbopropoxy, acetyl, carbamoyl, acetoxy, carboxy, hydroxy, amino, alkyl of 1 to 4 carbon atoms, alkoxy of 1 to 4 carbon atoms, or halo, (ii) pyridyl, (iii) pyrrolyl, (iv) imidazolyl, (v) naphthyl, (vi) thienyl, (vii) quinolyl, (viii) furyl, (ix) indolyl, or (x)

$$-N(R^{8'})(R^{9'})$$

in which $R^{8'}$ is hydrogen or alkyl of 1 to 4 carbon atoms, and $R^{9'}$ is hydrogen, alkyl of 1 to 4 carbon atoms, $COR^{10}$ or $-SO_2R^{10}$ in which $R^{10}$ is hydrogen alkyl of 1 to 4 carbon atoms, or phenyl; and n has a value of 1, 2, or 3.

Preferred compounds of Formula IB are those wherein $R^3$ is trifluoromethylphenyl, cyanophenyl, methoxyphenyl, fluorophenyl, or furyl, and n is 2.

A third preferred subclass pertains to compounds of the formula:

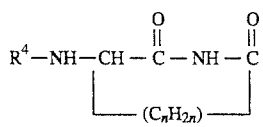  IC.

in which $R^4$ is alanyl, arginyl, glycyl, phenylglycyl, histidyl, leucyl, isoleucyl, lysyl, methionyl, prolyl, sarcosyl, seryl, homoseryl, threonyl, thyronyl, tyrosyl, valyl, benzimidol-2-yl, benzoxazol-2-yl, phenylsulfonyl, methylphenylsulfonyl, or phenylcarbamoyl, and n has a value of 1, 2, or 3.

Preferred compounds of Formula IC are those wherein $R^4$ is phenylsulfonyl or 2-amino-3-phenylpropanoyl and n is 2.

A second aspect of the present invention pertains to compounds of the formula:

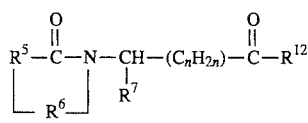  II.

in which $R^5$ is (i) o-phenylene, unsubstituted or substituted with nitro, cyano, trifluoromethyl, carbethoxy, carbomethoxy, carbopropoxy, acetyl, carbamoyl, acetoxy, carboxy, hydroxy, amino, alkyl of 1 to 4 carbon atoms, alkoxy of 1 to 4 carbon atoms, or halo, or (ii) the divalent residue of pyridine, pyrrolidine, imidizole, naphthalene, or thiophene, wherein the divalent bonds are on vicinal ring carbon atoms;

$R^6$ is —CO—, —CH$_2$—, or —SO$_2$—;

$R^7$ is (i) hydrogen, (ii) straight or branched alkyl of 1 to 6 carbon atoms, (iii) pyridyl, (iv) phenyl or phenyl substituted with one or two substituents selected from the group consisting of nitro, cyano, trifluoromethyl, carbethoxy, carbomethoxy, carbopropoxy, acetyl, carbamoyl, acetoxy, carboxy, hydroxy, amino, alkyl of 1 to 4 carbon atoms, alkoxy of 1 to 4 carbon atoms, or halo, (v) alkyl of 1 to 4 carbon atoms, (vi) benzyl unsubstituted or substituted with one or two substituents selected from the group consisting of nitro, cyano, trifluoromethyl, carbethoxy, carbomethoxy, carbopropoxy, acetyl, carbamoyl, acetoxy, carboxy, hydroxy, amino, alkyl of 1 to 4 carbon atoms, alkoxy of 1 to 4 carbon atoms, or halo, and (vi) —(C$_m$H$_{2m}$)—CO—R$^{11}$.

each of $R^{11}$ and $R^{12}$, independently of the other, is —OH or

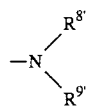

each of n and m, independently of the other, has a value of 0, 1, 2, or 3;

$R^{8'}$ is hydrogen or alkyl of 1 to 4 carbon atoms; and $R^{9'}$ is hydrogen, alkyl of 1 to 4 carbon atoms, —COR$^{10}$, or —SO$_2$R$^{10}$ in which is hydrogen, alkyl of 1 to 4 carbon atoms, or phenyl.

A first preferred subclass of Formula II pertains to compounds of the formula:

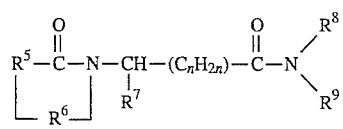  IIA.

in which $R^5$ is (i) o-phenylene, unsubstituted or substituted with nitro, cyano, trifluoromethyl, carbethoxy, carbomethoxy, carbopropoxy, acetyl, carbamoyl, acetoxy, carboxy, hydroxy, amino, alkyl of 1 to 4 carbon atoms, alkoxy of 1 to 4 carbon atoms, or halo, or (ii) the divalent residue of pyridine, pyrrolidine, imidizole, naphthalene, or thiophene, wherein the divalent bonds are on vicinal ring carbon atoms;

$R^6$ is —CO—, —CH$_2$—, or —SO$_2$—;

$R^7$ is (i) hydrogen, (ii) straight or branched alkyl of 1 to 6 carbon atoms, (iii) pyridyl, (iv) phenyl or phenyl substituted with one or two substituents selected from the group consisting of nitro, cyano, trifluoromethyl, carbethoxy, carbomethoxy, carbopropoxy, acetyl, carbamoyl, acetoxy, carboxy, hydroxy, amino, alkyl of 1 to 4 carbon atoms, alkoxy of 1 to 4 carbon atoms, or halo, (v) imidazol-4-yl-methyl, and (vi)

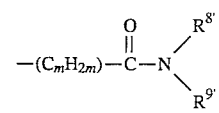

each of n and m, independently of the other, has a value of 0, 1, 2, or 3; each of $R^8$ and $R^{8'}$, independently of the other, is hydrogen or alkyl of 1 to 4 carbon atoms; and each of $R^9$ and $R^{9'}$, independently of the other, is hydrogen, alkyl of 1 to 4 carbon atoms, —COR$^{10}$ or —SO$_2$R$^{10}$ in which $R^{10}$ is hydrogen, alkyl of 1 to 4 carbon atoms, or phenyl.

Preferred compounds of Formula IIA are those in which $R^5$ is o-phenylene, $R^6$ is —CO—; $R^7$ is phenyl, substituted phenyl or pyridyl; n is 0 or 1, and each of $R^8$ and $R^9$ is hydrogen.

A second preferred subclass of Formula II pertains to compounds of the formula:

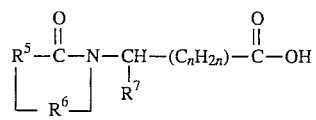  IIB.

in which $R^5$ is (i) o-phenylene, unsubstituted or substituted with nitro, cyano, trifluoromethyl, carbethoxy, carbomethoxy, carbopropoxy, acetyl, carbamoyl, acetoxy, carboxy, hydroxy, amino, alkyl of 1 to 4 carbon atoms, alkoxy of 1 to 4 carbon atoms, or halo, or (ii) the divalent residue of pyridine, pyrrolidine, imidizole, naphthalene, or thiophene, wherein the divalent bonds are on vicinal ring carbon atoms;

$R^6$ is —CO—, —CH$_2$—, or —SO$_2$—;

$R^7$ is (i) hydrogen, (ii) straight or branched alkyl of 1 to 6 carbon atoms, (iii) pyridyl, (iv) phenyl or phenyl substituted with one or two substituents selected from the group consisting of nitro, cyano, trifluoromethyl, carbethoxy, carbomethoxy, carbopropoxy, acetyl, carbamoyl, acetoxy, carboxy, hydroxy, amino, alkyl of 1 to 4 carbon atoms, alkoxy of 1 to 4 carbon atoms, or halo, (v) alkyl of 1 to 4 carbon atoms, (vi) benzyl unsubstituted or substituted with one or two substituents selected from the group consisting of nitro, cyano, trifluoromethyl, carbethoxy, carbomethoxy, carbopropoxy, acetyl, carbamoyl, acetoxy, carboxy, hydroxy, amino, alkyl of 1 to 4 carbon atoms, alkoxy of 1 to 4 carbon atoms, or halo, and (vi) —($C_mH_2m$)—CO-$R^{11}$ in which $R^{11}$ is —OH or

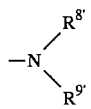

each of n and m, independently of the other, has a value of 0, 1, 2, or 3;

$R^{8'}$ is hydrogen or alkyl of 1 to 4 carbon atoms; and $R^{9'}$ is hydrogen, alkyl of 1 to 4 carbon atoms, —$COR^{10}$, or —$SO_2R^{10}$ in which $R^{10}$ is hydrogen, alkyl of 1 to 4 carbon atoms, or phenyl.

Preferred compounds of Formula IIB are those in which $R^5$ is o-phenylene, $R^6$ is —CO—; $R^7$ is phenyl, substituted phenyl or pyridyl; and n is 0 or 1.

Typical compounds of this invention include 2-(2,6-dioxo- 3-piperidinyl)-4-azaisoindoline-1,3-dione, 2-(2,6-dioxo-3-piperidinyl)-benzo[ e]isoindoline-1,3-dione, 5-(2,6-dioxo-3-piperidinyl)-pyrrolo[ 3,4-d]imidazole-4,6-dione, 3-(trifluoromethylphenylcarboxamido)piperidine- 2,6-dione,3-(cyanophenylcarboxamido) piperidine-2,6-dione, 3-(methoxyphenylcarboxamido) piperidine-2,6-dione, 3-(3-pyridylcarboxamido)-piperidine- 2,6-dione, 3- (2-furylcarboxamido) piperidine-2,6-dione, 3-phenylsulfonamidopiperidine-2,6-dione, 3-(2-amino- 3-phenylpropaneamido)-piperidine-2,6-dione, 2-phthalimido-2-phenylacetamide, 3-phthalimido-3-phenylpropanamide, 2-phthalimido-3-phenylpropanamide, 2-phthalimido-3-(4hydroxy)phenylpropanamide, 3-phthalimido-3-phenylpropionic acid, 2-phthalimido-2-(4-hydroxyphenyl)acetic acid, 2-phthalimido-2-phenylacetic acid, 2-phthalimido-2-(4-fluorophenyl)acetic acid, 2-phthalimido-2-(2-fluorophenyl)acetic acid, 2-phthalimido-2-(4-fluorophenyl)acetamide, 2-phthalimido- 3-phenylpropionic acid, 2-phthalimido-4-methylpentanoic acid, 3-phenylcarboxamidopiperidine-2,6-dione, 2-phthalimidoacetamide, 3-phthalimidopropanamide, 3-phthalimidoimidazoline- 2,5-dione, 3-phenylcarboxamidopropanamide, 2-phthalimido- 3-carbamoylpropionic acid, 2-(1,3-dioxo-4-azaisoindolinyl)- 3-carbamoylpropionic acid, 3-(1, 3-dioxo-4-azaisoindolinyl)piperidine- 2,6-dione, 2 -(1,3-dioxo-4-azaisoindolinyl)-acetamide, 3-phthalimido-3-carbamoylpropionic acid, 4-phthalimidobutyramide, and 4 -phthalimidobutyric acid.

The term alkyl as used herein denotes a univalent saturated branched or straight hydrocarbon chain. Unless otherwise stated, such chains can contain from 1 to 18 carbon atoms. Representative of such alkyl groups are methyl, ethyl, propyl, isopropyl, butyl, isobutyl, sec-butyl, tertbutyl, pentyl, isopentyl, neopentyl, tert-pentyl, hexyl, isohexyl, heptyl, octyl, nonyl, decyl, undecyl, dodecyl, tridecyl, tetradecyl, pentadecyl, hexadecyl, heptadecyl, octadecyl, and the like. When qualified by "lower", the alkyl group will contain fro 1 to 6 carbon atoms. The same carbon content applies to the parent term "alkane" and to derivative terms such as "alkoxy".

The compounds can be used, under the supervision of qualified professionals, to inhibit the undesirable effects of $TNF_\alpha$. The compounds can be administered orally, rectally, or parenterally, alone or in combination with other therapeutic agents including antibiotics, steroids, etc., to a mammal in need of treatment. Oral dosage forms include tablets, capsules, dragees, and similar shaped, compressed pharmaceutical forms. Isotonic saline solutions containing 20–100 mg/ml can be used for parenteral administration which includes intramuscular, intrathecal, intravenous and intraarterial routes of administration. Rectal administration can be effected through the use of suppositories formulated from conventional carriers such as cocoa butter.

Dosage regimens must be titrated to the particular indication, the age, weight, and general physical condition of the patient, and the response desired but generally doses will be from about 10 to about 500 mg/day as needed in single or multiple daily administration. In general, an initial treatment regimen can be copied from that known to be effective in interfering with $TNF_\alpha$ activity for other $TNF_\alpha$ mediated disease states by the compounds of the present invention. Treated individuals will be regularly checked for T cell numbers and T4/T8 ratios and/or measures of viremia such as levels of reverse transcriptase or viral proteins, and/or for progression of monokine-mediated disease associated problems such as cachexia or muscle degeneration. If no effect is soon following the normal treatment regimen, then the amount of monokine activity interfering agent administered is increased, e.g., by fifty percent a week.

The compounds of the present invention also can be used topically in the treatment or prophylaxis of topical disease states mediated or exacerbated by excessive $TNF_\alpha$ production, respectively, such as viral infections, such as those caused by the herpes viruses, or viral conjunctivitis, etc.

The compounds also can be used in the veterinary treatment of mammals other than in humans in need of inhibition of $TNF_\alpha$ production. $TNF_\alpha$ mediated diseases for treatment, therapeutically or prophylactically, in animals include disease states such as those noted above, but in particular viral infections. Examples include feline immunodeficiency virus, equine infectious anaemia virus, caprine arthritis virus, visna virus, and maedi virus, as well as other lentiviruses.

Certain of these compounds possess centers of chirality and can exist as optical isomers. Both the racemates of these isomers and the individual isomers themselves, as well as diastereomers when then are two chiral centers, are within the scope of the present invention. The racemates can be used as such or can be separated into their individual isomers mechanically as by chromatography using a chiral absorbant. Alternatively, the individual isomers can be prepared in chiral form or separated chemically from a mixture by forming salts with a chiral acid, such as the individual enantiomers of 10-camphorsulfonic acid, camphoric acid, alpha-bromocamphoric acid, methoxyacetic acid, tartaric acid, diacetyltartaric acid, malic acid, pyrrolidone- 5-carboxylic acid, and the like, and then freeing one or both of the resolved bases, optionally repeating the process, so as obtain either or both substantially free of the other; i.e., in a form having an optical purity of >95%.

The compounds can be prepared using methods which are known in general for the preparation of imides. However, the present invention also pertains to an improvement in the formation of the final compounds, as discussed below in greater detail.

An N-alkoxycarbonylimide and an amine thus are allowed to react in the presence of a base such as sodium carbonate or sodium bicarbonate substantially as described by Shealy et al., *Chem. & Ind.*, (1965) 1030–1031) and Shealy et al., *J. Pharm. Sci.* 57, 757–764 (1968) to yield the N-substituted imide. Alternatively, a cyclic acid anhydride can be reacted with an appropriate amine to form an imide. Formation of a cyclic imide also can be accomplished by refluxing a solution of an appropriately substituted dicarboxylic acid monoamide in anhydrous tetrahydrofuran with N,N'-carbonyldiimidazole. In contrast to prior art methods which produced a yield of less than 50%, this reaction produces yields in excess of 60%, in some cases greater than 90%. This reaction also has broader applicability, being useful not only in the preparation of compounds of the present invention but also in the preparation of known compounds such as thalidomide.

Inhibition of $TNF_\alpha$ by these compounds can be conveniently assayed using anti-$TNF_\alpha$ antibodies. For example, plates (Nunc Immunoplates, Roskilde, DK) are treated with 5 μg/mL of purified rabbit anti-$TNF_\alpha$ antibodies at 4° C. for 12 to 14 hours. The plates then are blocked for 2 hours at 25° C. with PBS/0.05% Tween containing 5 mg/mL BSA. After washing, 100 μL of unknowns as well as controls are applied and the plates incubated at 4° C. for 12 to 14 hours. The plates are washed and assayed with a conjugate of peroxidase (horseradish) and mouse anti-$TNF_\alpha$ monoclonal antibodies, and the color developed with o-phenylenediamine in phosphatecitrate buffer containing 0.012% hydrogen peroxide and read at 492 nm.

The following examples will serve to further typify the nature of this invention but should not be construed as a limitation in the scope thereof, which scope is defined solely by the appended claims.

EXAMPLE 1

A stirred suspension of (S)-glutamine (14.6 g, 100 mmol) and 2,3-pyridinedicarboxylic anhydride (14.9 g, 100 mmol) in 100 mL of acetic acid is heated and refluxed for 1 hour. The reaction solution is cooled to form a solid. The solid is removed by filtration and washed with acetic acid to yield 7.11 g (26%) of 2-(1,3-dioxo-4-azaisoindolin-2yl)glutaramic acid. The product can be further purified by slurring in 700 mL of refluxing ethanol, cooling, filtering, and drying to produce a white powder with a melting point of 222°–226° C.; $^1$H NMR (DMSO-$d_6$) δ 13.25 (br s, 1 H, COOH), 9.04 (dd, 1 H, J=1.2, 4.9 Hz, pyr), 8.37 (dd, 1 H, J = 1.2, 7.8 Hz, pyr), 7.85 (dd, 1 H, J=4.9, 7.8 Hz, pyr), 7.20 (s, 1 H, $CONH_2$), 6.73 (s, 1 H, $CONH_2$), 4.83 (dd, 1 H, J=10.2, 4.8 Hz, CHN), 2.55–1.90 (m, 4 H, $CH_2CH_2$); $^{13}$C NMR (DMSO-$d_6$) δ1173.22, 170.21, 165.8, 165.7, 155.4, 150.9, 131.7, 128.3, 126.9, 51.5, 31.4, 24.0.

Utilization of asparagine in place of glutamine produces 2-(1,3-dioxo-4-azaisoindolin-2-yl)-malonamic acid.

By substituting equivalent amounts of 2,3-naphthalenedicarboxylic anhydride and 4,5-imidazoledicarboxylic anhydride for 2,3-pyridinedicarboxylic anhydride in the foregoing procedure, there are respectively obtained 2-(1,3-dioxobenzo[e]isoindolin-2-yl)glutaramic acid and 2-(4,6-dioxopyrrolo[3,4-d]imidazol-5-yl)glutaramic acid.

EXAMPLE 2

A stirred suspension of 1.39 g, 5.01 mmol, of 2-(1,3-dioxo- 4-azaisoindolin-2-yl)glutaramic acid (see Example 1), N,N'-carbonyldiimidazole (0.890 g, 5.49 mmol) and N,N-dimethylaminopyridine (0.005 g, 0.04 mmol) in 20 mL of tetrahydrofuran is refluxed for 15 hours. The reaction slurry is cooled and the solid removed by filtration and washed with minimal tetrahydrofuran. 2-(2,6-Dioxo-3-piperidinyl)- 4-azaisoindoline-1,3-dione (0.859 g, 66%) is recovered as a white powder. $^1$H NMR (DMSO-d6) 6 11.18 (s, 1 H, NHCO), 9.04 (d, 1 H, J=5.0 Hz, pyr), 8.39 (d, 1 H, J= 7.7 Hz, pyr), 7.86 (dd, 1 H, J=5.0, 7.7 Hz, pyr), 5.25 (dd, 1 H, J=15.3, 13 Hz, 1 H, CHCO) , 3.05–2.75 (m, 1 H, $CH_2CO$), 2.75 (m, 2 H, $CH_2CO$, $CH_2$), 2.20–2.00 (m, 1 H, $CH_2CO$, $CH_2$); $^{13}$C NMR (DMSO-d6) 6 172.6, 169.6, 165.4, 155.3, 150.8, 131.7, 128.2, 126.9, 49.0, 30.8, 21.8. Anal. Calcd for $Cl_2H_9N_3O_4$. Theory 55.60, 3.50, 16.21. Found 55.50, 3.53, 16.11.

Substitution of 2-(1,3-dioxo-4-azaisoindolin-2-yl)malonamic acid in the foregoing procedure yields 2-(2,5-dioxo-3-pyrrolidinyl)-4-azaisoindoline-1,3-dione.

By substituting equivalent amounts of 2-(1,3-dioxobenzo[e]isoindolin-2-yl)glutaramic acid and 2-(4,6-dioxopyrrolo[3,4-d]imidazol-5-yl)glutaramic acid in the foregoing procedure, there are respectively obtained 2-(2,6-dioxo- 3-piperidinyl)-benzo[e]isoindoline-1,3-dione and 5-( 2,6-dioxo-3-piperidinyl)-pyrrolo[3,4-d]imidazole-4,6-dione.

EXAMPLE 3

A solution of L-glutamine (2.92 g, 20.0 mmoL) and sodium hydroxide (20 mmoL) in water is added to a stirred solution of phenylisocyanate (2.4 g, 2.2 mL, 20 mmoL) in acetonitrile (40 mL). The reaction mixture is stirred for 45 hours and is partially concentrated to remove acetonitrile. The reaction mixture is washed with ethyl acetate (2 x 25 mL each). The pH of the reaction mixture is adjusted to 1–2 with 4N hydrochloric acid. The slurry of the reaction mixture is filtered and the solid washed and dried to yield 4.70 g of N-phenyl-N'-(4-carboxybutyramide)urea (89%) as a white powder.

By substituting 4-trifluoromethylphenylisocyanate, 3-cyanophenylisocyanate, 2-methoxyphenylisocyanate, fur-2-ylisocyanate, and pyrid-3-ylisocyanate for phenylisocyanate in the foregoing procedure, there are respectively obtained N-(4-trifluoromethylphenyl)-N'-(4-carboxybutyramide)urea, N-( 3-cyanophenyl)-N'-(4-carboxybutyramide)urea, N-(2-methoxy-phenyl)-N' -(4-carboxybutyramide)urea, N-(fur-2-yl)-N'-(4-carboxybutyramide)urea, and N-(pyrid-3-yl)-N'-(4-carboxybutyramide)urea.

EXAMPLE 4

N-Phenyl-N'-(4-carboxybutyramide)urea (2.00 g, 7.54 mmoL) is mixed with carbonyldiimidazole (1.24 g, 7.95 mmoL) in tetrahydrofuran (30 mL) is heated and refluxed for 16 hours. The reaction mixture is concentrated and the residue slurried in water (25 mL). The resulting slurry is filtered and the solid is washed with water and air dried to yield 0.63 g of 3-phenylcarboxamidopiperidine-2,6-dione which can be alternatively named as N-phenyl-N'-(2-glutarimide)urea as a white flocculent powder. After being allowed to stand, the filtrate is refiltered to yield 0.70 g of additional material. $^1$H NMR (DMSO-$d_6$) 6 8.51 (s, 1H, CONHCO), 7.6–7.2 (m, 6 H, Ar, ArNH), 6.83 (s, 1 H, NHCH), 4.26 (t, 1 H, CHCO), 2.4–1.8 (m, 4 H, $CH_2CH_2$); $^{13}$C NMR (DMSO-$d_6$) δ 173.2, 155.6,, 132.2, 128.7, 127.7, 126.7, 55.7, 29.8, 27.2. Anal. Calcd for $C_{12}H_{13}N_3O_3$. Theoretical: C, 58.29; H, 5.29; N, 16.99. Found: C, 58.12; H, 5.17; N, 17.02.

By substituting N-(4-trifluoromethylphenyl)-N'-(4-carboxybutyramide)urea, N-(3-cyanophenyl)-N'-(4-carboxybutyramide)urea, N-(2-methoxyphenyl)-N'-(4-carboxybutyramide)urea, N-(fur-2-yl)-N'-(4-carboxybutyramide)urea, and N-(pyrid- 3-yl)-N'-(4-carboxybutyramide)urea for N-phenyl-N'-( 4-carboxybutyramide)urea in the foregoing procedure, there are respectively obtained 3-(4-trifluoromethylphenylcarboxamido)piperidine- 2,6-dione, 3-(3-cyanophenylcarboxamido)-piperidine- 2,6-dione, 3-(2-methoxyphenylcarboxamido)piperidine- 2,6-dione, 3-(fur-2-ylcarboxamido)piperidine-2,6-dione, and 3-(pyrid-3- ylcarboxamido)piperidine-2,6-dione.

EXAMPLE 5

To a stirred mixture of phenylglycine (3.0 g, 20 mmoL) and sodium carbonate (2.23 g, 21 mmoL) in 450 mL of water is added N-carbethoxyphthalimide (4.38 g, 20 mmoL). After 45 minutes, the reaction slurry is filtered. The filtrate is stirred and the pH adjusted to 1–2 with 4 N hydrochloric acid. After 1 hour, the resulting slurry is filtered and the solid washed with water. The solid is dried in vacuo (60° C., <1 mm) to afford 2.88 g (51%) of 2-phthalimido-2-phenylacetic acid, which can be alternatively named as N-phthaloylphenylglycine, as a white powder.

Use of β-phenyl-β-alanine, β-phenyl-β-alanine, histidine, and tyrosine in place of phenylglycine in the procedure of this example yields respectively 3-phthalimido-3-phenylpropionic acid, 2-phthalimido-3-phenylpropionic acid, 2-phthalimido-3-imidazolylpropionic acid, and 2-phthalimido- 3-(4-hydroxyphenyl)propionic acid.

EXAMPLE 6

To a stirred mixture of 2-phthalimido-2-phenylacetic acid (2.50 g, 8.89 mmoL) in tetrahydrofuran (50 mL) is added carbonyldiimidazole (1.50 g, 9.25 mmoL) and a few crystals of 4-dimethylaminopyridine. The reaction is then heated to 50° C. for 45 minutes. After the reaction mixture cools to room temperature, 1 mL of concentrated ammonium hydroxide is added via syringe. The reaction is stirred for 1 hour, then diluted with 50 mL of water and partially concentrated to remove the majority of the tetrahydrofuran. The resulting slurry is filtered and the solid washed with copious amounts of water. The solid is dried in vacuo (60° C., <1 mm) to afford 1.9 g (76%) of 2-phthalimido-2-phenylacetamide, which may be alternatively named as N-phthaloylphenylglycinamide, as an off-white powder: mp 218°–220½° C.; $^1$H NMR (DMSO-d$_6$) δ 9.00–7.75 (m, 4 H, Ar), 7.61 (br s, 1 H, CONH$_2$), 7.55–7.20 (m, 6 H, Ar, CONH$_2$), 5.82 (s, 1 H, CHCO$_2$); $^{13}$C NMR (DMSO-d$_6$) δ 168.2, 167.1, 135.6, 134.5, 131.4, 129.4, 127.9, 127.7, 123.1, 56.3. Anal ($C_{16}H_{12}N_2O_3$), C, H, N.

Use of 3-phthalimido-3-phenylpropionic acid, 2-phthalimido- 3-phenylpropionic acid, 2-phthalimido-3-imidazolylpropionic acid, and 2-phthalimido-3-(4-hydroxyphenyl)propionic acid in place of 2-phthalimido-2-phenylacetic acid in the procedure of this example yields respectively 3-phthalimido- 3-phenylpropanamide, 2-phthalimido-3-phenylpropanamide, 2-phthalimido-3-imidazolylpropanamide, and 2-phthalimido- 3-(4-hydroxy)phenylpropanamide.

EXAMPLE 7

To a stirred mixture of β-alanine (4.45 g, 50.0 mmoL) and sodium carbonate (5.35 g, 50.5 mmoL) in 100 mL of water is added N-carbethoxyphthalimide (10.95 g, 50.0 mmoL). After 1.5 hour, the reaction slurry is filtered. The filtrate is stirred and the pH adjusted to 1–2 with 4N hydrochloric acid. After 15 minutes, the resulting slurry is filtered and the solid washed with water. The solid is dried in vacuo (60° C., <1 mm) to afford 6.96 g (64%) of N-phthaloyl-β-alanine, which can be alternatively named as 3-phthalimidopropionic acid, as a white powder.

EXAMPLE 8

To a stirred solution of N-phthaloyl-β-alanine (2.19 g, 10.0 mmoL) in tetrahydrofuran (25 mL) is added carbonyldiimidazole (1.62 g, 10.0 mmoL) and a few crystals of 4-N,N-dimethylaminopyridine followed by 15 mL of tetrahydrofuran. The reaction is then heated to 40°–45° C. for 1 hour. After the reaction mixture cools to room temperature, 1 mL of concentrated ammonium hydroxide is added via syringe. The reaction is stirred for 20 minutes and the resulting slurry filtered and the solid washed with tetrahydrofuran. The solid is dried in vacuo (60° C., <1 mm) to afford 1.72 g (79%) of N-phthaloyl-β-alanine amide, which can be alternatively named as 3-phthalimidopropanamide, as a white powder: mp 252°–253° C.; $^1$H NMR (DMSO-d6) δ 8.00–7.70 (m, 4 H, Ar), 7.45 (br s, 1 H, CONH$_2$), 6.89 (br s, 1 H, CONH$_2$), 3.78 (t, 2 H, J=7 Hz, CH$_2$CO), 2.43 (t, 2 H, CH$_2$); $^{13}$C NMR (DMSO-d$_6$) δ 171.5, 167.6, 134.2, 131.6, 122.9, 34.1, 33.5. Anal. Calcd for $C_{11}H_{10}N_2O_3$. Theoretical: C, 60.55; H, 4.62; N, 12.84. Found: C, 60.49; H, 4.59; N, 12.82.

EXAMPLE 9

To a stirred solution of glycinamide hydrochloride (2.20 g, 20.0 mmoL) and sodium carbonate (2.54 g, 24 mmoL) in 25 mL of water is added N-carbethoxyphthalimide (4.38 g, 20.0 mmoL). The resulting suspension is stirred for 1.5 hour and then filtered to afford 3.22 g (79%) of the crude product as a white powder. The crude product is slurried in 200 mL of refluxing ethanol. The resulting suspension after cooling to room temperature is filtered and the solid dried in vacuo (60° C., <1 mm) to afford 2.65 g (65%) of N-phthaloylglycinamide as a white powder: mp 199°–201° C.; $^1$H NMR (DMSO-d$_6$) δ 8.00–7.8 (m, 4 H, Ar), 7.70 (br s, 1 H, CONH$_2$), 7.26 (br s, 1 H, CONH$_2$), 4.16 (s, 2 H, CH$_2$); $^{13}$C NMR (DMSO-d$_6$) δ 167.8, 167.5, 134.4, 131.7, 123.1, 39.9. Anal. Calcd for $C_{11}H10N_2O_3$. Theoretical: C, 60.55; H, 4.62; N, 12.84. Found: C, 60.49; H, 4.59; N, 12.82.

EXAMPLE 10

To a stirred solution of L-glutamine (43.8 g, 300 mmoL) and sodium carbonate (33.4 g, 315 mmoL) in 750 mL of water is rapidly added N-carbethoxyphthalimide [65.8 (97% pure, 67.8 g), 300 mmoL] as a solid. After 1 hour, the reaction mixture is filtered to remove unreacted N-carbethoxyphthalimide. The pH of the stirred filtrate is adjusted to 3–4 with 4N hydrochloric acid. The mixture is then seeded with N-phthaloyl-L-glutamine and the pH adjusted to 1–2 with 4N hydrochloric acid. The resulting slurry is stirred for 1 hour. The slurry is filtered and the solid washed with copious amounts of water. The solid is air-dried and then dried in vacuo (60° C., <1 mm) overnight to afford 49.07 g (59%) of N-phthaloyl-L-glutamine, which can be alternatively named as 2-phthalimidoglutaramic acid, as a white powder.

EXAMPLE 11

A stirred mixture of N-phthaloyl-L-glutamine (48.0 g, 174 mmoL), carbonyldiimidazole (30.43 g, 188 mmoL), and 4-dimethylaminopyridine (0.105 g, 0.861 mmoL) in anhydrous tetrahydrofuran (300 mL) is heated to reflux for 16 hours. The reaction slurry is filtered and the solid washed with methylene chloride (200 mL). The solid is air-dried and then dried in vacuo (60° C., <1 mm) to afford 40.40 g (90%) of thalidomide as a white powder. $^1$H NMR (DMSO-d$_6$) δ

11.16 (s, 1 H, NH), 8.05–7.80 (br s, 4 H, Ar), 5.18 (dd, 1 H, J=12, 5 Hz, CHCO), 3.05–2.85 (m, 1 H, CH$_2$CO), 2.70–2.45 (m, 2 H, CH$_2$CH$_2$), 2.15–2.00 (M, 1 H, CH$_2$). $^{13}$C NMR (DMSO-d$_6$) δ 172.8, 169.8, 167.1, 134.9, 131.2, 123.4, 49.0, 30.9, 22.0.

EXAMPLE 12

A stirred suspension of (S)-glutamine (14.6 g, 100 mL) and pyridine-2,3-dicarboxylic anhydride (14.9 g, 100 mmol) in 100 mL of acetic acid is heated at reflux for 1 hour. The resulting solution is allowed to cool. The solid which forms upon cooling is filtered and the solid washed with acetic acid and dried to afford 7.11 g (26%) of crude product. The crude product is slurried in 700 mL of refluxing ethanol, the suspension cooled, and the slurry collected by filtration and dried to afford 6.10 g (23%) of N-quinolinylglutamine, which can be alternatively named as 2-(1,3-dioxo-4-azaisoindol- 2-yl)-3-carbamoylpropionic acid, as a white powder. mp 222°–226° C.; $^1$H NMR (dmso-d$_6$) δ 13.25 (br s, 1 H, COOH), 9.04 (dd, 1 H, J=1.2, 4.9 Hz, pyr), 8.37 (dd, 1 H, J=1.2, 7.8 Hz, pyr), 7.85 (dd, 1 H, J=4.9, 7.8 Hz, pyr), 7.20 ( s, 1 H, CONH$_2$), 6.73 ( s, 1 H, CONH$_2$), 4.83 (dd, 1 H, J=10.2, 4.8 HZ, CHN), 2.55–1.90 (m, 4 H, CH$_2$CH$_2$); $^{13}$C NMR (dmso-d$_6$) δ 1173.22, 170.21, 165.8, 165.7, 155.4, 150.9, 31.7, 128.3, 126.9, 51.5, 31.4, 24.0.

EXAMPLE 13

A stirred suspension of N-quinolinylglutamine (1.39 g, 5.01 mmol), carbonyldiimidazole (0.890 g, 5.49 mmol), and N,N-dimethylpyridine (0.005 g, 0.04 mmol) in 20 mL of tetrahydrofuran is heated at reflux for 15 hours. After cooling, the reaction slurry is filtered and the solid washed with minimal tetrahydrofuran to afford, after drying 0.859 g (66%) of N-quinolinylglutarimide, which can be, alternatively named as 3-(1,3-dioxo-4-azaisoindol-2-yl)-2,6-dioxopiperidine, as a white powder: $^1$H NMR (dmso-d$_6$) δ 11.18 (s, 1 H, NHCO), 9.04 (d, 1 H, J=5.0 Hz, pyr), 8.39 (d, 1 H, J=7.7 Hz, pyr), 7.86 (dd, 1 H, J=5.0, 7.7 Hz, pyr), 5.25 (dd, 1 H, J=15.3 , 13 Hz, 1 H, CHCO), 3.05–2.75 (m, 1 H, CH$_2$CO), 2.75 (m, 2 H, CH$_2$CO, CH$_2$), 2.20–2.00 (m, 1 H, CH$_2$CO, CH$_2$); $^{13}$C NMR (dmso-d$_6$) δ 172.6, 169.6, 165.4, 155.3, 150.8, 131.7, 128.2, 126.9, 49.0, 30.8, 21.8. Anal. Calculated for C$_{12}$H$_9$N$_3$O$_4$. Theory 55.60, 3.50, 16.21. Found 55.50, 3.53, 16.11.

EXAMPLE 14

To a stirred mixture of phenylglycine (3.0 g, 20 mmol) and sodium carbonate (2.23 g, 21 mmol) in 450 mL of water is added N-carbethoxyphthalimide (4.38 g, 20 mmol). After 45 minutes, the reaction slurry is filtered. The filtrate is stirred and the pH adjusted to 1–2 with 4N hydrochloric acid. After 1 hour, the resulting slurry is filtered and the solid washed with water. The solid is dried in vacuo (60° C., <1 mm) to afford 2.88 g (51%) of 2-phthalimidophenylacetic acid as a white powder.

By employing (R)-phenylglycine, there is obtained (R) 2-phthalimido-phenylacetic acid, as a white powder: mp 175°– 177° C.; $^1$H NMR (dmso-d$_6$, 250 M Hz) δ 12.50 (br s, 1H), 7.95– 7.85 (m, 4H), 7.55–7.28 (m, 5H), 6.04 ( s, 1H); $^{13}$C NMR (dmso-d$_6$) δ 168.9, 166.9, 135.0, 134.9, 131.0, 129.1, 128.1, 127.9, 123.5, 56.1. Anal. Calculated for C$_{16}$H$_{11}$NO$_4$. Theoretical: C, 68.32; H, 3.94; N, 4.98. Found: C, 68.32; H, 3.85; N, 4.95.

Likewise from (S)-phenylglycine, there is obtained (S)-2-phthalimido-phenylacetic acid as a white powder: mp 180°– 184° C.; $^1$H NMR (dmso-d$_6$, 250 M Hz) δ 12.5 (br s, 1H), 7.95 7.85 (m, 4H) , 7.55–7.28 (m, 5H) , 6.04 ( s, 1H); $^{13}$C NMR (dmso-d$_6$) δ 168.9, 166.9, 135.0, 134.9, 130.9, 129.1, 128.1, 127.9, 123.5, 55.1. Anal. Calculated for C$_{16}$H$_{11}$NO$_4$. Theoretical: C, 68.32; H, 3.94; N, 4.98. Found: C, 68.14; H, 3.87; N, 4.96.

EXAMPLE 15

To a stirred solution of N-phthaloylglycine (2.50 g, 8.89 mmol) in tetrahydrofuran (50 mL) is added carbonyldiimidazole (1.50 g, 9.25 mmol) and a few crystals of 4-N,N-dimethylaminopyridine. The reaction is then heated to 50° C. for 45 minutes. After the reaction mixture had cooled to room temperature, 1 mL of concentrated ammonium hydroxide is added via syringe. The reaction is stirred for 1 hour, then diluted with 50 mL of water and partially concentrated to remove the majority of the tetrahydrofuran. The resulting slurry was filtered and the solid washed with copious amounts of water. The solid was dried in vacuo (60° C., 1 mm) to afford 1.9 g (76%) of 2-phthalimido-2-phenylacetamide as an off-white powder: mp 218°–220° C.; $^1$H NMR (dmso-d$_6$) δ 9.00–7.75 (m, 4 H, Ar), 7.61 (br s, 1 H, CONH$_2$), 7.55–7.20 (m, 6 H, Ar, CONH$_2$), 5.82 (s, 1 H, CHCO$_2$); $^{13}$C NMR (dmso-d$_6$) δ 168.2, 167.1, 135.6, 134,5, 131.4, 129.4, 127.9, 127.7, 123.1, 56.3.

EXAMPLE 16

To a stirred mixture of β-alanine (4.45 g, 50.0 mmol) and sodium carbonate (5.35 g, 50.5 mmol) in 100 mL of water is added N-carbethoxyphthalimide (10.95 g, 50.0 mmol). After 1.5 hour, the reaction slurry is filtered. The filtrate is stirred and the pH adjusted to 1–2 with 4N hydrochloric acid. After 15 minutes, the resulting slurry is filtered and the solid washed with water. The solid is dried in vacuo (60° C., <1 mm) to afford 6.96 g (64%) of N-phthaloyl-β -alanine, which can be alternatively named as 3-phthalimido- 3-phenylpropionic acid, as a white powder.

EXAMPLE 17

To a stirred solution of N-phthaloyl-β-alanine (2.19 g, 10.0 mmol) in tetrahydrofuran (25 mL) is added carbonyldiimidazole (1.62 g, 10.0 mmol) and a few crystals of 4-N,N-dimethylaminopyridine, followed by 15 mL of tetrahydrofuran. The mixture is heated at 40°–45° C. for 1 hour. After the reaction mixture is cooled to room temperature, 1 mL of concentrated ammonium hydroxide is added via syringe. The reaction is stirred for 20 minutes and the resulting slurry is filtered and the solid washed with tetrahydrofuran. The solid is dried in vacuo (60° C., < 1 mm) to afford 1.72 g (79%) of N-phthaloyl-β-alanine amide, which can be alternatively named as 3-phthalimidopropionic acid, as a white powder: mp 252°–253° C.; $^1$H NMR (dmso-d$_6$) δ 8.00–7.70 (m, 4 H, Ar), 7.45 (br s, 1 H, CONH$_2$), 6.89 (br s, 1 H, CONH$_2$), 3.78 ( t, 2 H, J=7 Hz, CH$_2$CO), 2.43 (t, 2 H, CH$_2$); $^{13}$C NMR (dmso-d$_6$) δ 171.5, 167.6, 134.2, 131.6, 122.9, 34.1, 33.5. Anal. Calculated for C$_{11}$H$_{10}$N$_2$O$_3$. Theoretical: C, 60.55; H, 4.62; N, 12.84. Found: C, 60.49; H, 4.59; N, 12.82.

EXAMPLE 18

To a stirred solution of glycinamide hydrochloride (2.20 g, 20.0 mmol) and sodium carbonate (2.54 g, 24 mmol) in 25 mL of water is added N-carbethoxyphthalimide (4.38 g, 20.0 mmol). The resulting suspension is stirred for 1.5 hour and then filtered to afford 3.22 g (79%) of crude product as a white powder. The crude product is slurried in 200 mL of refluxing ethanol and, after cooling to room temperature, the resulting suspension is filtered and the solid dried in vacuo (60° C., <1 mm) to afford 2.65 g (65%) of N-phthaloylglycinamide, which can be alternatively named as phthalimidoacetamide, as a white powder: mp 199°–201° C.; 1H NMR (dmso-$d_6$) δ 8.00–7.8 (m, 4 H, Ar), 7.70 (br s, 1 H, $CONH_2$), 7.26 (br s, 1 H, $CONH_2$), 4.16 (s, 2 H, $CH_2$); $^{13}C$ NMR (dmso-$d_6$) δ 167.8, 167.5, 134.4, 131.7, 123.1, 39.9. Anal. Calculated for $C_{11}H_{10}N_2O_3$. Theoretical: C, 60.55; H, 4.62; N, 12.84. Found: C, 60.49; H, 4.59; N, 12.82.

EXAMPLE 19

By following the procedure of Example 17 but utilizing an equivalent amount of 4-aminobutyric acid, there is obtained a 67% yield of 4-phthalimidobutyric acid as a white powder: mp 108°–111° C.; $^1H$ NMR (dmso-$d_6$) δ 12.10 (s, 1 H),, 7.92°–7.75 (m, 4 H, Ar), 3.62 (t, J=6.8 Hz, 2 H), 2.29 (t, J=7.2 Hz, 2 H), 1.90–1.76 (m, 2 H); $^{13}C$ NMR (dmso-$d_6$) δ 173.8, 167.9, 134.2, 131.6, 122.9, 36.8, 30.9, 23.3.

EXAMPLE 20

By following the procedure of Example 15 but utilizing an equivalent amount of 4-phthalimidobutyric acid, there is obtained 4-phthalimidobutyramide as a white powder in a 23% yield: mp 159.5°–161.5° C.; $^1H$ NMR (dmso-$d_6$) δ 8.0–7.7 (m, 4 H, Ar), 3.58 (t, J=6.9 Hz, 2 H), 2.09 (t, 2 H), 1.92–1.70 (m, 2 H); $^{13}C$ NMR (dmso-$d_6$) 6 173.3, 167.9, 134.2, 131.6, 122.9, 37.1. 32.3, 23.9.

Example 21

By following the procedure of Example 18 but employing N-carbethoxyphthalimide and (S)-phenylalaninamide hydrochloride, there is obtained (S)-2-phthalimido-3-phenylpropionamide which can be recrystallized from ethanol to afford white crystals: mp 211°–215° C.; $^1H$ NMR (dmso-$d_6$) δ 7.92 (s, 5 H, Ph), 7.72, 7.33 (2 s, 2 H), 7.2–7.0 (m, 4 H, Ar), 4.92 (dd, 1 H, J=12, 4.5 Hz), 3.52 (dd, 1 H, J=4.3, 13.9), 3.35 (dd, 1 H, J=12, 13.9); $^{13}C$ NMR (dmso-$d_6$) δ 169.6, 167.4, 137.7, 134.3, 131.2, 128.5, 128.1, 126.3, 122.9, 54.2, 33.7.

EXAMPLE 22

To a stirred solution of d,l-phenylalanine (4.17 g, 25.0 mmol) and sodium carbonate (2.78 g, 26.25 mmol) in 50 mL of water is added N-carboethoxyphthalimide (5.65 g, 25.0 mmol). The resulting slurry is stirred for 1.5 hour and filtered. The pH of the filtrate is adjusted to 1–2 with 4 N hydrochloric acid with stirring. After 20 minutes, the slurry is refiltered and the solid washed with water. The solid is dried in vacuo (60° C., <1 mm) to afford 5.44 g (74%) of 2-phthalimido-3-phenylpropionic acid as a white powder: mp 165°–169° C.; $^1H$ NMR (dmso-$d_6$, 250 M Hz) δ 12.5(br s, 1H), 7.84(s, 4H), 7.23–7.06 (m, 5H), 5.13 (dd, 1H, J=5.0) , 3.26–3.05 (m, 2H); $^{13}C$ NMR (250 MHz, dmso-$d_6$) δ 170.0, 167.0, 137.2, 134.8, 130.6, 128.6, 128.2, 126.5, 123.3, 52.8, 33.8. Anal. Calculated for $C_{17}H_{13}NO_4$. Theoretical: C, 69.15; H, 4.44; N, 4.74. Found: C, 69.07; H, 4.34; N, 4.78.

EXAMPLE 23

To a stirred solution of 2-phthalimido-3-phenylpropionic acid (2.95 g, 10.0 mmol) in tetrahydrofuran (25 mL) are added carbonyldiimidazole (1.62 g, 10.0 mmol) and a few crystals of 4-N,N-dimethylaminopyridine, followed by 15 mL of tetrahydrofuran. The reaction mixture is stirred at room temperature for 45 minutes and 1 mL of concentrated ammonium hydroxide then is added. After 10 minutes, the reaction mixture is diluted with 50 mL water and the resulting slurry is partially concentrated to remove the tetrahydrofuran and filtered. The solid is washed with water and dried in vacuo (60° C., <1 mm) to afford 2.46 g (84%) of 2-phthalimido- 3-phenylpropionamide as a white powder: mp 224°– 226° C.; $^1H$ NMR (dmso-$d_6$, 250 MHz) δ 7.79 (s, 4 H, Ar), 7.71 (br s, 1 H, $CONH_2$), 7.32 (br s, 1 H, $CONH_2$), 7.20–7.02 (m. 5H, Ar) , 5.06–4.98 (m, 1H ) , 3.56–3.25 (m, 2H); $^{13}C$ NMR (dmso-$d_6$, 250 MHz) δ: 169.6, 168.0, 137.1, 134.3, 131.2, 129.5, 128.1, 126.3, 122.9, 54.2, 33.7. Anal. Calculated for $C_{17}H_{14}N_2O_3$. Theoretical: C, 69.38; H,4.79; N, 9.52. Found: C, 69.37; H, 4.73; N, 9.43.

EXAMPLE 24

To a stirred solution of 4-fluorophenyglycine (3.38 g, 20.0 mmol) and sodium carbonate in 450 mL of 2:1 water:acetonitrile is added N-carbethoxyphthalimide (4.38 g, 20 mmol). After 1 hour, the reaction mixture is partially concentrated to remove the acetonitrile. The resulting slurry is filtered and the pH of the stirred filtrate is adjusted to 1–2 with 4 N hydrochloric acid and then stirred for an additional 30 minutes and filtered. The solid is air-dried and then dried in vacuo (60° C., < 1 mm) to afford 4.55 g (76%) of 2-phthalimido-2-(4-fluorophenyl)acetic acid as a white powder: mp 180°–183° C.; $^1H$ NMR (dmso-$d_6$, 250 MHz) δ 8.10–7.80 (m, 4 H), 7.65–7.45 (m, 4 H), 7.3–7.10 (t, 2 H), 6.10 (s, 1 H); $^{13}C$ NMR (dmso-$d_6$, 250 MHz) δ168.9, 166.9, 163.6, 159.7, 135.0, 131.4, 131.3 (m), 130.9, 123.5, 115.0, 114.7, 54.4. Anal. Calculated for $C_{16}H_{10}NO_4F$. Theoretical: C, 64.22; H, 3.37; N, 4.68. Found: C, 64.13; H, 3.33; N, 4.63.

Similarly prepared from 2-fluorophenylglycine is 2-phthalimido- 2-(2-fluorophenyl)acetic acid as a white solid: mp 174.5°–180.5° C.; $^1H$ NMR (dmso-$d_6$) δ 13.8 (br s, 1 H), 7.65– 7.15 (m, 4H), 6.18 (s, 1 H); $^{13}C$ NMR (dmso-$d_6$) δ 168.1, 166.8, 162.1, 158.2, 135.0, 130.9, 130.8, 130.5, 130.4, 124.1. 123.6, 121.8, 121.6, 115.3, 114.9, 48.9. Anal. Calculated for $C_{16}H_{10}NO_4F$. Theoretical: C, 64.22; H, 3.37; N, 4.68. Found: C, 63.93; H, 3.27; N, 4.68.

EXAMPLE 25

Similarly prepared according to the procedure of Example 23 from 2-phthalimido-2-(4-fluorophenyl)acetic acid, carbonyldiimidazole, 4-N,N-dimethylaminopyridine and concentrated ammonium hydroxide is 2-phthalimido-2-(4-fluorophenyl)acetamide which can be recrystallized from tetrahydrofuran to afford 0.76 g (51%) of the product as white crystals: mp 180°–183° C.; $^1H$ NMR (dmso-$d_6$) δ 8.00–7.55 (m, 4 H), 7.64 (s, 1 H), 7.60–7.40 (m, 3 H), 7.25–7.05 (m, 2 H), 5.83 (s, 1 H). Anal. Calculated for $C_{16}H_{11}N_2O_3F$. Theoretical: C, 64.43; H, 3.72; N, 9.39. Found: C, 64.16; H, 3.62; N, 9.18.

Likewise from 2-phthalimido-2-(2-fluorophenyl)acetic acid there is obtained 2-phthalimido-2-(2-fluorophenyl)acetamide as small white crystals: mp 197°–201° C.; 1H NMR (dmso-$d_6$) δ 8.05–7.75 (m, 5 H), 7.65–7.05 (m, 5 H), 6.06 (s, 1 H), $^{13}C$ NMR (dmso-$d_6$) δ 167.4, 166.9, 162.2, 158.3, 134.6, 131.3, 131.2, 131.1, 130.2, 130.0, 123.9, 123.8, 123.2, 122.4, 115.1, 114.8, 49.9.

EXAMPLE 26

To a stirred solution of d,l-leucine (3.31 g, 25.0 mmol) and sodium carbonate (2.78 g, 26.25 mmol) in 50 mL of water is added N-carboethoxyphthalimide (5.65 g, 25.0 mmol). After 1 hour at room temperature, the reaction slurry is filtered, the filtrate stirred, and the pH adjusted to 1–2 with 4N hydrochloric acid. The mixture is stirred overnight, the resulting slurry is filtered, and the solid washed with water and dried in vacuo (60° C., <1 mm) to afford 5.32 g (81%) of the 2-phthalimido-4-methylpentanoic acid as a white powder: mp 134°–137° C.; $^1$H NMR (dmso-d$_6$, 250 M Hz) δ 12.50 (br s, 1H), 8.00–7.80 (m, 4H), 4.79 (dd, 1H, J=4.3), 2.28–2.10 (m, 1H), 1.94–1.77 (m, 1H), 1.51–1.34 (m, 1H), 0.89 (d, 3H, J=4.4), 0.86 (d, 3H, J=4.5); $^{13}$C NMR (dmso-d$_6$) δ 170.8, 167.4, 134.8, 131.1, 123.3, 50.2, 36.7, 24.6, 23.0, 20.8. Anal. Calculated for $C_{14}H_{15}NO_4$. Theoretical: C, 64.36; H, 5.74; N, 5.36. Found: C, 64.18; H, 5.73; N, 5.98.

EXAMPLE 27

To a stirred solution of 2-phthalimido-4-methylpentanoic acid (1.32 g, 5.0 mmol) in tetrahydrofuran (25 mL) are added carbonyldiimidazole (0.81 g, 5.0 mmol) and a few crystals of 4-N,N-dimethylaminopyridine followed by 15 mL of tetrahydrofuran. The reaction mixture is stirred at room temperature for 1 hour, then 1 mL of concentrated ammonium hydroxide is added. After 10 minutes, the reaction mixture is diluted with 50 mL water. The resulting slurry is partially concentrated to remove the tetrahydrofuran and filtered. The solid is washed with water and dried in vacuo (60° C., <1 mm) to afford 1.16 g (89%) of 2-phthalimido-4-methylpentanamide as a white powder: mp 173°–176° C.; $^1$H NMR (dmso-d$_6$, 250 MHz) δ 7.95–7.79 (m, 4 H, Ar), 7.61 (br s, 1 H, CONH$_2$), 7.22 (br s, 1 H, CONH$_2$), 4.73–4.60 (m, 1 H), 2.30–2.10 (m, 1 H), 1.95–1.80 (m, 1H), 1.45–1.25 (m, 1H); $^{13}$C NMR (dmso-d$_6$) δ: 170.4, 167.7, 134.4, 131.5, 123.1, 51.3, 36.4, 24.7, 23.2, 20.6. Anal. Calculated for $C_{14}H_{16}N_2O_3$. Theoretical: C, 64.60; H, 6.20; N, 10.76. Found: C, 64.63; H, 6.11; N, 10.70.

EXAMPLE 28

To a stirred solution of histidine (3.17 g, 20.0 mmol) and sodium carbonate (2.23 g, 21 mmol) in 50 mL of water is added N-carboethoxyphthalimide (4.52 g, 20.0 mmol). After 1.5 hour, the reaction slurry is filtered. The filtrate is stirred and the pH adjusted to 1–2 with 4N hydrochloric acid. The resulting slurry is filtered and the solid washed with water and dried in vacuo (60 C, <1 mm) to afford 3.65 g (64%) of 2-phthalimido-3-(imidazol-4-yl)propionic acid as a white powder: mp 280°–285° C.; $^1$H NMR (dmso-d$_6$, 250 M Hz) δ 12.5 (br s, 1H), 7.90–7.60 (m, 6H), 6.80(s, 1H), 4.94 (t, 1H, J=7.8), 3.36 (d, 2H, J=7.8); $^{13}$C NMR (dmso-d$_6$) δ 170.1, 167.1, 134.8, 134.6, 133.2, 131.1, 123.2, 116.3, 52.4, 25.8; Anal. Calculated for $C_{14}H_{11}N_3O_4$. Theoretical: C, 58.95; H, 3.89; N, 14.73. Found: C, 58.80; H, 3.88; N, 14.66.

EXAMPLE 29

To a stirred mixture of 3-amino-3-(4-methoxyphenyl)propionic acid (1.95 g, 10.0 mmol) and sodium carbonate (1.11 g, 10.5 mmol) in 200 mL of acetonitrile-water 1:1 is added N-carboethoxyphthalimide (2.26 g, 10.0 mmol). After 1 hour, the reaction slurry is filtered. The filtrate is concentrated to remove the acetonitrile and the pH adjusted to 1–2 with 4 N hydrochloric acid and stirred over night. The resulting slurry is filtered and the solid washed with water. The solid is dried in vacuo (60 C, <1 mm) to afford 2.82 g (87%) of the 3-phthalimido-3-(4-methoxyphenyl)propionic acid as a white powder: mp 160°–164° C.; $^1$H NMR (dmso-d$_6$, 250 MHz) δ 12.5 (br s, 1H), 7.95–7.80 (m, 4 H), 7.36 (d, 2 H, J=8.7), 6.92 (d, 2 H, J=8.4 Hz), 5.18–5.10 (m, 1 H), 3.70–3.15 (m, 2 H); $^{13}$C NMR (dmso-d$_6$) δ 171.7, 167.6, 158.6, 134.6, 131.0, 130.8, 128.3, 123.1, 113.9, 55.0, 49.6, 35.9. Anal. Calculated for $C_{18}H_{15}NO_5$. Theoretical: C, 66.46; H, 4.63; N, 4.31. Found: C, 66.25; H, 4.65; N, 4.28.

Similarly from 3-amino-3-(3-methoxyphenyl)propionic acid there is obtained 3-phthalimido-3-(3-methoxyphenyl)propionic acid as white crystals: mp 111°–115° C.; $^1$H NMR (dmsod$_6$, 250 MHz) 6 12.5 (br s, 1H), 7.94–7.81 (m, 4 H), 7.32– 7.23 (m, 1H), 7.02–6.85 (m, 3 H), 5.70–5.60 (m, 1 H), 3.77– 3.67 (s, 3H), 3.56–3.15 (m, 2 H); $^{13}$C NMR (dmso-d$_6$) δ 171.6, 167.6, 159.2, 140.4, 134.7, 131.0, 129.7, 123.2, 119.0, 112.9, 112.7, 54.9, 50.0, 35.8.

Likewise from 3-amino-3-(2-methoxyphenyl)propionic acid there is obtained 3-phthalimido-3-(2-methoxyphenyl)propionic acid as a white powder: mp 163°–168 ° C.; $^1$H NMR (dmso-d$_6$, 250 MHz) δ 12.5 (br s, 1H), 7.95–7.80 (m, 4 H), 7.45–6.90 (m, 4H), 6.05–5.92 (m, H), 3.78 (s, 3H) 3.55–3.05 (m, 2 H); $^{13}$C NMR (dmso-d$_6$) 171.7, 167.5, 156.1, 134.5, 131.0, 128.9, 127.3, 126.1, 123.0, 120.1, 111.0, 55.5, 45.3, 35.1.

EXAMPLE 30

By following the procedure of Example 27 utilizing 3-phthalimido- 3-(4-methoxyphenyl)propionic acid, there is obtained 3-phthalimido-3-(4-methoxyphenyl)propionamide as a white powder: mp 183°–188° C.; $^1$H NMR (dmso-d$_6$, 250 MHz) δ 7.90–7.75 (m, 4 H, Ar), 7.58 (br s, 1 H, CONH$_2$), 7.38 (d, 2H, J=8.6 ), 6.91 (d, 3H, J=8.6), 5.73 (t, 1H, J=7.8), 3.23(d, 2H, J=7.9); $^{13}$C NMR (dmso-d$_6$) δ: 171.2, 167.6, 158.5, 134.5, 131.3, 131.2, 128.4, 123.0, 113.7, 55.0, 49.9, 36.8.. Anal. Calculated for $C_{18}H_{16}N_2O_4$. Theoretical: C, 66.66; H,4.97; N, 8.64. Found: C, 66.27; H, 5.04; N, 8.40.

EXAMPLE 31

To a stirred mixture of 3-amino-3-(4-cyanophenyl)propionic acid (3.80 g, 20.0 mmol) and sodium carbonate (2.23 g, 21 mmol) in 100 mL of water is added N-carboethoxyphthalimide (4.52 g, 20.0 mmol). After 2 hour, the reaction slurry is filtered and the pH of the stirred filtrate adjusted to 1–2 with 4 N hydrochloric acid. The resulting gel is extracted with ethyl acetate (3×30 mL). The extract is dried over magnesium sulfate and concentrated in vacuo. The crude product is recrystallized from 10% aqueous acetonitrile and then recrystallized from 20% aqueous methanol. The product is dried in vacuo (60° C., <1 mm) to afford 1.5 g (23%) of 3-phthalimido-3-(4-cyanophenyl)propionic acid as a white powder: mp 134°–137° C.; $^1$H NMR (dmso-d$_6$, 250 MHz) δ 12.5 (br s, 1H), 7.95–7.56 (m, 8 H),.5.76 (t, 1 H, J=7.7), 3.57–3.15 (m, 2 H); $^{13}$C NMR (dmso-d$_6$) δ 171.5, 167.6, 144.2, 134.8, 132.6, 131.1, 128.1, 123.3, 118.5, 49.7, 35.5.

Likewise from 3-amino-3-(3-cyanophenyl)propionic acid there is obtained 3-phthalimido-3-(3-cyanophenyl)propionic acid as a white powder: mp 172°–175° C.; $^1$H NMR (dmso-d$_6$, 250 MHz) δ 12.5 (br s, 1H), 8.05–7.51 (m, 8 H), 5.82–5.70 (m, 1 H), 3.63–3.20(m, 2 H); $^{13}$C NMR (dmso-d$_6$) δ 171.5, 167.6, 140.3, 134.6 132.0, 131.5, 131.2, 130.7, 129.8, 123.22, 118.5, 111.6, 49.3, 35.6.

EXAMPLE 32

By following the procedure of Example 27 utilizing 3-phthalimido- 3-(4-cyanophenyl)propionic acid, there is obtained 3-phthalimido-3-(4-cyanophenyl)propionamide as a white powder: $^1$H NMR (dmso-d$_6$, 250 MHz) δ 8.05–7.50 (m, 9 H), 6.97 (s, 1 H), 5.87–5.72 (m, 1 H), 3.44–3.12 (m, 2 H); $^{13}$C NMR (dmso-d$_6$) δ 170.8, 167.6, 144.6, 134.6, 132.4, 131.1, 127.9, 123.2, 118.5, 110.3, 49.8, 36.4.

Similarly from 3-phthalimido-3-(3-cyanophenyl) propionic acid (1.60 g, 5.0 mmol), there is obtained 3-phthalimido- 3-(3-cyanophenyl)propionamide as a white powder: mp 217°– 220° C.; $^1$H NMR (dmso-d$_6$, 250 MHz) δ 8.05–7.40 (m, 9 H), 6.99 (br s, 1 H), 5.90–5.75 (m, 1H ), 3.50–3.10 (m, 2H); $^{13}$C NMR (dmso-d$_6$) δ: 171.0, 167.7, 140.8, 134.6, 132.2, 131.5, 131.4, 130.8, 129.9, 123.2, 118.7,111.5, 49.7, 36.7.

EXAMPLE 33

To a stirred solution of phenyl isocyanate (2.2 mL, 2.4 g, 20 mmol) in acetonitrile (40 mL) is added a solution of L-glutamine (2.92 g, 20.0 mmol) and sodium hydroxide (20 mmol) in water (20 mL). The reaction mixture is stirred for 45 hours, partially concentrated to remove the acetonitrile, and washed with ethyl acetate (2×25 mL). The pH of the aqueous layer is adjusted to 1–2 with 4N hydrochloric acid, the resulting thick slurry filtered, and the solid washed with water and air-dried to afford 4.70 g (89%) yield of 2-(N-phenyluriedo)- 4-carbamoylbutyric acid as a white powder.

2-(N-phenyluriedo)-4-carbamoylbutyric acid (2.00 g, 7.54 mmol) and carbonyldiimidazole (1.24 g, 7.95 mmol) in tetrahydrofuran (30 mL) are heated at reflux for 16 hours. The reaction mixture is concentrated and the residue slurried in water (25 mL), the slurry filtered, and the solid washed with water and air-dried to afford 0.63 g of N-phenyl-N' -(1,6-dioxopiperidin-2-yl)urea. After sitting, filtration of the filtrate afforded 0.70 g (38%) of the product as a white flocculent powder: $^1$H NMR (dmso-d$_6$) δ 8.51 (s, 1 H, CONHCO), 7.6–7.2 (m, 6 H, Ar, ArNH), 6.83 (s, 1 H, NHCH), 4.26 (t, 1 H, CHCO), 2.4–1.8 (m, 4 H, CH$_2$CH$_2$); $^{13}$C NMR (dmso-d$_6$) δ 173.2, 155.6, 132.2, 128.7, 127.7, 126.7, 55.7, 29.8, 27.2. Anal. Calculated for C$_{12}$H$_{13}$N$_3$O$_3$. Theoretical: C, 58.29; H, 5.29; N, 16.99. Found: C, 58.12; H, 5.17; N, 17.02.

EXAMPLE 34

Tablets, each containing 50 mg of active imide ingredient, can be prepared in the following manner:

| Constituents (for 1000 tablets) | |
| --- | --- |
| active imide ingredient | 50.0 g |
| lactose | 50.7 g |
| wheat starch | 7.5 g |
| polyethylene glycol 6000 | 5.0 g |
| talc | 5.0 g |
| magnesium stearate | 1.8 g |
| demineralised water | q.s. |

The solid ingredients are first forced through a sieve of 0.6 mm mesh width. The active imide ingredient, the lactose, the talc, the magnesium stearate and half of the starch then are mixed. The other half of the starch is suspended in 40 ml of water and this suspension is added to a boiling solution of the polyethylene glycol in 100 ml of water. The resulting paste is added to the pulverulent substances and the mixture is granulated, if necessary with the addition of water. The granulate is dried overnight at 35° C., forced through a sieve of 1.2 mm mesh width and compressed to form tablets of approximately 6 mm diameter which are concave on both sides.

EXAMPLE 35

Tablets, each containing 100 mg of active imide ingredient, can be prepared in the following manner:

| Constituents (for 1000 tablets) | |
| --- | --- |
| active imide ingredient | 100.0 g |
| lactose | 100.0 g |
| wheat starch | 47.0 g |
| magnesium stearate | 3.0 g |

All the solid ingredients are first forced through a sieve of 0.6 mm mesh width. The active imide ingredient, the lactose, the magnesium stearate and half of the starch then are mixed. The other half of the starch is suspended in 40 ml of water and this suspension is added to 100 ml of boiling water. The resulting paste is added to the pulverulent substances and the mixture is granulated, if necessary with the addition of water. The granulate is dried overnight at 35° C., forced through a sieve of 1.2 mm mesh width and compressed to form tablets of approximately 6 mm diameter which are concave on both sides.

EXAMPLE 36

Tablets for chewing, each containing 75 mg of active imide ingredient, can be prepared in the following manner:

| Composition (for 1000 tablets) | |
| --- | --- |
| active imide ingredient | 75.0 g |
| mannitol | 230.0 g |
| lactose | 150.0 g |
| talc | 21.0 g |
| glycine | 12.5 g |
| stearic acid | 10.0 g |
| saccharin | 1.5 g |
| 5% gelatin solution | q.s. |

All the solid ingredients are first forced through a sieve of 0.25 mm mesh width. The mannitol and the lactose are mixed, granulated with the addition of gelatin solution, forced through a sieve of 2 mm mesh width, dried at 50° C. and again forced through a sieve of 1.7 mm mesh width. The active imide ingredient, the glycine and the saccharin are carefully mixed, the mannitol, the lactose granulate, the stearic acid and the talc are added and the whole is mixed thoroughly and compressed to form tablets of approximately mm diameter which are concave on both sides and have a breaking groove on the upper side.

EXAMPLE 37

Tablets, each containing 10 mg of active imide ingredient, can be prepared in the following manner:

| Composition (for 1000 tablets) | |
| --- | --- |
| active imide ingredient | 10.0 g |
| lactose | 328.5 g |
| corn starch | 17.5 g |
| polyethylene glycol 6000 | 5.0 g |
| talc | 25.0 g |
| magnesium stearate | 4.0 g |
| demineralised water | q.s. |

The solid ingredients are first forced through a sieve of 0.6 mm mesh width. Then the active imide ingredient, lactose, talc, magnesium stearate and half of the starch are intimately mixed. The other half of the starch is suspended in 65 ml of water and this suspension is added to a boiling solution of the polyethylene glycol in 260 ml of water. The resulting paste is added to the pulverulent substances, and the whole is mixed and granulated, if necessary with the addition of water. The granulate is dried overnight at 35° C., forced through a sieve of 1.2 mm mesh width and compressed to form tablets of approximately 10 mm diameter which are concave on both sides and have a breaking notch on the upper side.

EXAMPLE 38

Gelatin dry-filled capsules, each containing 100 mg of active imide ingredient, can be prepared in the following manner:

| Composition (for 1000 capsules) | |
|---|---|
| active imide ingredient | 100.0 g |
| microcrystalline cellulose | 30.0 g |
| sodium lauryl sulphate | 2.0 g |
| magnesium stearate | 8.0 g |

The sodium lauryl sulphate is sieved into the active imide ingredient through a sieve of 0.2 mm mesh width and the two components are intimately mixed for 10 minutes. The microcrystalline cellulose is then added through a sieve of 0.9 mm mesh width and the whole is again intimately mixed for 10 minutes. Finally, the magnesium stearate is added through a sieve of 0.8 mm width and, after mixing for a further 3 minutes, the mixture is introduced in portions of 140 mg each into size 0 (elongated) gelatin dry-fill capsules.

EXAMPLE 39

A 0.2% injection or infusion solution can be prepared, for example, in the following manner:

| | |
|---|---|
| active imide ingredient | 5.0 g |
| sodium chloride | 22.5 g |
| phosphate buffer pH 7.4 | 300.0 g |
| demineralised water | to 2500.0 ml |

The active imide ingredient is dissolved in 1000 ml of water and filtered through a microfilter. The buffer solution is added and the whole is made up to 2500 ml with water. To prepare dosage unit forms, portions of 1.0 or 2.5 ml each are introduced into glass ampoules (each containing respectively 2.0 or 5.0 mg of imide).

What is claimed is:

1. In the process of preparing thalidomide in which N-phthaloylisoglutamine or N-phthaloylglutamine is cyclized with N-N'-carbonyldiimidazole, the improvement which comprises cyclizing said N-phthaloylisoglutamine or N-phthaloylglutamine by refluxing a mixture of N-phthaloylisoglutamine or N-phthaloylglutamine, N-N'-carbonyldiimidazole and anhydrous tetrahydrofuran.

* * * * *